(12) United States Patent
Molas et al.

(10) Patent No.: US 7,278,988 B2
(45) Date of Patent: Oct. 9, 2007

(54) DUAL-USE PANTILINER

(75) Inventors: Horacio Jorge Molas, Buenos Aires (AR); Franz Aschenbrenner, Kastl (DE); Holger Gerlach, Erlangen (DE); Melanie Hufnagel, Erlangen (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 120 days.

(21) Appl. No.: 09/957,109

(22) Filed: Sep. 20, 2001

(65) Prior Publication Data

US 2002/0077614 A1 Jun. 20, 2002

Related U.S. Application Data (63) Continuation-in-part of application No. 09/741,486, filed on Dec. 18, 2000, now abandoned, and a continuation-in-part of application No. 09/738,077, filed on Dec. 15, 2000, now abandoned.

(51) Int. Cl.
*A61F 13/474* (2006.01)
*A61F 13/45* (2006.01)
*A61F 13/535* (2006.01)
*A61F 13/536* (2006.01)

(52) U.S. Cl. .................. 604/385.201; 604/385.01; 604/387; 604/380

(58) Field of Classification Search ........ 604/327–332, 604/346–349, 365–366, 309, 379–380, 385.01, 604/385.03–385.05, 385.101, 385.14, 385.17, 604/385.19, 386, 387, 393–396, 385.201 604/354–355
See application file for complete search history.

(56) References Cited

U.S. PATENT DOCUMENTS

| | | |
|---|---|---|
| 2,408,508 A | 10/1946 | Canavan |
| 3,802,817 A | 4/1974 | Matsuki et al. ............... 425/66 |
| 3,849,241 A | 11/1974 | Butin et al. ................. 161/169 |
| 3,855,046 A | 12/1974 | Hansen et al. .............. 161/150 |
| 3,881,490 A | 5/1975 | Whitehead et al. |
| 4,059,114 A | 11/1977 | Richards |
| 4,100,324 A | 7/1978 | Anderson et al. ........... 428/288 |
| 4,285,343 A | 8/1981 | McNair |
| 4,333,466 A | 6/1982 | Matthews |
| 4,340,563 A | 7/1982 | Appel et al. ................ 264/518 |
| 4,347,092 A | 8/1982 | Hlaban et al. .............. 156/227 |
| 4,536,181 A | 8/1985 | Cook ......................... 604/387 |

(Continued)

FOREIGN PATENT DOCUMENTS

DE 1 170 581 10/1955

(Continued)

OTHER PUBLICATIONS

English translation of Danish Patent Application No. PA 199900013.

*Primary Examiner*—Karin M. Reichle
(74) *Attorney, Agent, or Firm*—Ralph H. Dean, Jr.; Randall W Fieldback (57) ABSTRACT

A pantiliner has a periphery and at least one fold line. The fold line allows the pantiliner to be adjusted in size by folding the pantiliner along the fold line(s). The product is thus convertible and may be used with conventional "hourglass" shaped panties or folded along the fold lines to fit thong panties.

18 Claims, 4 Drawing Sheets

U.S. PATENT DOCUMENTS

| | | | |
|---|---|---|---|
| 4,589,876 A | 5/1986 | Van Tilburg | |
| 4,627,848 A | 12/1986 | Lassen et al. | 604/370 |
| 4,631,062 A * | 12/1986 | Lassen et al. | 604/385.02 |
| 4,640,810 A | 2/1987 | Laursen et al. | 264/518 |
| 4,743,245 A | 5/1988 | Lassen et al. | |
| 4,758,240 A | 7/1988 | Glassman | |
| 4,790,838 A | 12/1988 | Pigneul et al. | |
| 4,804,380 A | 2/1989 | Lassen et al. | |
| 4,818,464 A | 4/1989 | Lau | 264/510 |
| 4,946,454 A | 8/1990 | Schmidt | |
| 4,950,264 A * | 8/1990 | Osborn, III | 604/385.08 |
| 5,037,417 A | 8/1991 | Ternstrom et al. | |
| 5,171,302 A * | 12/1992 | Buell | 604/369 |
| 5,197,959 A | 3/1993 | Buell | |
| 5,275,591 A | 1/1994 | Mavinkurve | |
| 5,277,976 A | 1/1994 | Hogle et al. | 428/397 |
| 5,284,703 A | 2/1994 | Everhart et al. | 428/283 |
| 5,383,868 A | 1/1995 | Hyun | |
| 5,429,630 A | 7/1995 | Beal et al. | |
| D366,524 S | 1/1996 | Chung | D24/125 |
| D368,519 S | 4/1996 | Harrison et al. | D24/125 |
| 5,591,150 A * | 1/1997 | Olsen et al. | 604/385.23 |
| 5,683,373 A | 11/1997 | Darby | |
| 5,704,928 A * | 1/1998 | Morita et al. | 604/387 |
| 5,704,929 A | 1/1998 | Bien | |
| 5,713,886 A | 2/1998 | Sturino | |
| 5,729,835 A | 3/1998 | Williams | 2/406 |
| D394,503 S | 5/1998 | Perrini | D24/125 |
| D395,504 S | 6/1998 | Darby | D24/125 |
| D395,508 S | 6/1998 | Darby | D24/125 |
| D398,397 S | 9/1998 | Raidel | D24/125 |
| 5,827,251 A | 10/1998 | Moder et al. | 604/358 |
| D401,327 S | 11/1998 | Raidel | D24/125 |
| 5,830,296 A * | 11/1998 | Emenaker et al. | 156/219 |
| 5,891,127 A | 4/1999 | Moder et al. | 604/358 |
| D411,006 S | 6/1999 | Nixon et al. | |
| 5,964,741 A | 10/1999 | Moder et al. | 604/358 |
| 5,986,165 A | 11/1999 | Moder et al. | 604/358 |
| D425,985 S | 5/2000 | Velazquez et al. | D24/125 |
| D425,986 S | 5/2000 | Velazquez et al. | D24/125 |
| D426,304 S | 6/2000 | Mitchler et al. | D24/125 |
| D426,889 S | 6/2000 | Bissah et al. | |
| D430,292 S | 8/2000 | Orschel et al. | |
| D434,145 S | 11/2000 | Sugahara | |
| 6,160,197 A | 12/2000 | Lassen et al. | 604/358 |
| D439,057 S | 3/2001 | Bissah et al. | |
| 6,284,943 B1 * | 9/2001 | Osborn et al. | 604/366 |
| D454,195 S | 3/2002 | Kitzinger et al. | |
| 6,416,502 B1 * | 7/2002 | Connelly et al. | 604/387 |
| 6,443,934 B1 | 9/2002 | Glaug et al. | |
| 6,503,233 B1 * | 1/2003 | Chen et al. | 604/385.01 |
| 2002/0077613 A1 * | 6/2002 | Molas | |
| 2002/0077618 A1 * | 6/2002 | Molas | |
| 2002/0128622 A1 | 9/2002 | Carvalho et al. | |

FOREIGN PATENT DOCUMENTS

| | | |
|---|---|---|
| DE | 295 13 548 | 2/1996 |
| DE | 296 00 384 | 6/1996 |
| DE | 296 14 542 * | 2/1997 |
| DE | 296 14 542 U1 | 2/1997 |
| DE | 299 04 464 | 7/1999 |
| DE | 198 37 090 | 2/2000 |
| DE | 299 21 095 | 5/2000 |
| DE | 299 23 050 | 5/2000 |
| DE | 200 02 192 | 6/2000 |
| DE | 199 03 109 | 8/2000 |
| DE | 200 00 451 | 8/2000 |
| DE | 299 23 333 U1 | 9/2000 |
| DE | 299 11 806 | 12/2000 |
| DE | 199 31 283 | 1/2001 |
| DE | 100 31 352 | 6/2001 |
| DE | 200 22 170 | 9/2001 |
| DE | 101 44 908 | 10/2002 |
| EP | 0405403 | 1/1991 |
| EP | 0 511 905 | 11/1992 |
| EP | 0 523 107 | 2/1995 |
| EP | 0 958 800 | 11/1999 |
| EP | 1 138 294 | 10/2001 |
| EP | 1 245 209 | 10/2002 |
| GB | 2076491 | 11/1998 |
| GB | 2087071 | 12/1999 |
| GB | 2093492 | 6/2000 |
| GB | 2093048 | 12/2000 |
| GB | 2097389 | 12/2000 |
| GB | 2097390 | 12/2000 |
| GB | 2100609 | 4/2001 |
| GB | 2100610 | 4/2001 |
| GB | 2100611 | 4/2001 |
| GB | 2100612 | 4/2001 |
| GB | 2100613 | 4/2001 |
| GB | 2100614 | 4/2001 |
| GB | 2100615 | 4/2001 |
| GB | 2100616 | 4/2001 |
| GB | 2098936 | 11/2001 |
| GB | 2104737 | 11/2002 |
| GB | 2106982 | 11/2002 |
| GB | 2106983 | 11/2002 |
| GB | 2106987 | 11/2002 |
| GB | 2106988 | 11/2002 |
| GB | 2106989 | 11/2002 |
| GB | 2106990 | 11/2002 |
| WO | WO 9311725 A1 * | 6/1993 |
| WO | 94/02098 | 2/1994 |
| WO | WO 9507674 A1 * | 3/1995 |
| WO | WO 9515139 A1 * | 6/1995 |
| WO | 97/39713 | 10/1997 |
| WO | 98/22058 | 5/1998 |
| WO | 98/51249 | 11/1998 |
| WO | 00/30585 | 6/2000 |
| WO | 00/42963 | 7/2000 |
| WO | 00/59426 | 10/2000 |
| WO | 00/72790 | 12/2000 |
| WO | 0132118 | 5/2001 |
| WO | 01/67982 | 9/2001 |
| WO | 01/68024 | 9/2001 |
| WO | 01/78636 | 10/2001 |
| WO | 01/78638 | 10/2001 |
| WO | 01/78639 | 10/2001 |
| WO | 02/45636 | 6/2002 |
| WO | 02/054999 | 7/2002 |

* cited by examiner

DUAL-USE PANTILINER

This application is a continuation-in-part of application Ser. No. 09/741,486 entitled "Dual-Use Pantiliner" and filed in the U.S. Patent and Trademark Office on Dec. 18, 2000 and application Ser. No. 09/738,077 entitled "Dual-Use Pantiliner" and filed in the U.S. Patent and Trademark Office on Dec. 15, 2000 both now abandoned. The entirety of application Ser. No. 09/741,486 and application Ser. No. 09/738,077 are hereby incorporated by reference.

BACKGROUND OF THE INVENTION

The present invention concerns feminine hygiene products, more particularly, pantiliners made to protect women's underwear from staining.

Pantiliners are a class of feminine napkin designed to absorb minimal amounts of fluid. They are smaller and more compact than conventional sanitary napkins. These products are designed to be flexible and soft and to protect the panties of the wearer from staining. Traditional pantiliners are shaped like an elongated oval and cover the panty in the perineal area. Novel designs for panties make traditional pantiliner designs less well suited for use with them. The newly popular "thong" panty, in particular, is unsuited for use with elongated-oval pantiliners. Thong panties have a narrowed rear portion that is not as wide as the elongated-oval pantiliner.

Pantiliners are available in shapes specifically designed for thong panties, and the elongated-oval pantiliner is still available. A consumer wanting the ability to choose either type of panty and protect it with the appropriately shaped liner currently must choose between the various pantiliner shapes. If she has panties of varying shapes she must also have pantiliners of matching shapes. This involves dedicating storage space for and purchasing two differently shaped pantiliners. A single pantiliner product, easily convertible from one shape to another would, therefore, reduce the space requirement and money spent by the consumer.

There remains a need, therefore, for a pantiliner product that may be used by a wearer to protect panties having different designs. This would allow the consumer a simpler choice to cover her needs and reduce the storage space and monetary expenditure required of the consumer for these products.

SUMMARY OF THE INVENTION

In response to the discussed difficulties and problems encountered in the prior art, a new pantiliner including a liner, a baffle, and absorbent core between the liner and baffle, has been developed wherein the pantiliner has a periphery and at least one fold line defining a central area and two side areas. The pantiliner may be adjusted in size by folding the pantiliner along the fold line. The fold lines are lines of embossing which do not penetrate the baffle, and may be produced at between about 40 and 80° C. The pantiliner has an absorbent core, preferably between 50 and 200 gsm, with regard to basis weight, which may be made from spunbond webs, meltblown webs, bonded-carded webs, airlaid webs, and laminates and composites thereof.

In another aspect of the invention, the pantiliner may have side areas that are thinner than the central area.

In a more particular embodiment, the pantiliner has a liquid permeable liner, a liquid impervious baffle, and an absorbent core positioned therebetween. The absorbent core is made of more than 70 weight percent pulp hydroentangled with spunbond polypropylene fibers. The pantiliner has a periphery and at least one embossed fold line, which does not penetrate the baffle, and may be adjusted in size by folding said pantiliner along said embossed fold line.

The liquid impervious baffle helps keep liquid from passing through the pantiliner and staining the clothing of the wearer. The baffle may be breathable.

Various treatments may be applied to the pantiliner to improve fluid transfer, improve the environment near the skin or to actually improve skin health.

DEFINITIONS

"Disposable" includes being disposed of after a single use and not intended to be washed and reused.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

"Spunbonded fibers" refers to small diameter fibers that are formed by extruding molten thermoplastic material as filaments from a plurality of fine capillaries of a spinneret. Such a process is disclosed in, for example, U.S. Pat. No. 4,340,563 to Appel et al. and U.S. Pat. No. 3,802,817 to Matsuki et al. The fibers may also have shapes such as those described, for example, in U.S. Pat. No. 5,277,976 to Hogle et al. which describes fibers with unconventional shapes.

As used herein "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 19% bond area. Typically, the percent bonding area varies from around 10% to around 30% of the area of the fabric laminate web. As in well known in the art, the spot bonding holds the laminate layers together as well as imparts integrity to each individual layer by bonding filaments and/or fibers within each layer.

As used herein, the term "coform" means a process in which at least one meltblown diehead is arranged near a chute through which other materials are added to the web while it is forming. Such other materials may be pulp, superabsorbent particles, natural polymers (for example, rayon or cotton fibers) and/or synthetic polymers (for example, polypropylene or polyester) fibers, for example, where the fibers may be of staple length. Coform processes are shown in commonly assigned U.S. Pat. No. 4,818,464 to Lau and U.S. Pat. No. 4,100,324 to Anderson et al. Webs produced by the coform process are generally referred to as coform materials.

"Bonded carded web" refers to webs that are made from staple fibers which are sent through a combing or carding unit, which separates or breaks apart and aligns the staple fibers in the machine direction to form a generally machine direction-oriented fibrous nonwoven web. This material may be bonded together by methods that include point bonding, through air bonding, ultrasonic bonding, adhesive bonding, etc.

"Airlaying" is a well-known process by which a fibrous nonwoven layer can be formed. In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another using, for example, hot air or a spray adhesive. Airlaying is taught in, for example, U.S. Pat. No. 4,640,810 to Laursen et al.

"Personal care product" means products for the absorption of body exudates, such as diapers, training pants, disposable swim wear, absorbent underpants, adult incontinence products, bandages, veterinary and mortuary products, and feminine hygiene products like sanitary napkins and pantiliners.

"Target area" refers to the area or position on a personal care product where an insult is normally delivered by a wearer.

DETAILED DESCRIPTION OF THE INVENTION

Modern sanitary napkins and other personal care products usually have an outer cover, an inner core portion and a liner that goes against the wearer's skin.

The outer cover or "baffle" is designed to be impermeable to liquid in order to keep the clothing or bedding of the wearer from becoming soiled. The impermeable baffle is preferably made from a thin film and is generally made from plastic though other materials may be used. Nonwoven webs, films or film coated nonwovens may be used as the baffle as well. Suitable film compositions for the baffle include polyethylene film which may have an initial thickness of from about 0.5 mil (0.012 millimeter) to about 5.0 mil (0.12 millimeter). The baffle may optionally be composed of a vapor or gas permeable, microporous "breathable" material, that is permeable to vapors or gas yet substantially impermeable to liquid. Breathability can be imparted in polymer films by, for example, using fillers in the film polymer formulation, extruding the filler/polymer formulation into a film and then stretching the film sufficiently to create voids around the filler particles, thereby making the film breathable. Generally, the more filler used and the higher the degree of stretching, the greater the degree of breathability. Other suitable thermoplastic materials like other olefins, nylons, polyesters or copolymers of, for example, polyethylene and polypropylene may also be used.

The liner is designed to be highly permeable to liquid and to be non-irritating to the skin. Such a liner allows urine and menses to penetrate through itself quite easily and feels soft to the skin. The liner may be made from various materials including nonwoven webs, apertured films, foams and combinations thereof. The nonwovens and films may be made from synthetic polymers similar to the baffle, including polyolefins like polyethylene and polypropylene. The nonwovens may also be made from natural fibers or combinations of natural and synthetic fibers. Liners may also be made from creped materials such as creped nonwoven webs.

The liner may optionally have more than one layer or may have one layer in a central area with multiple layers in the side areas. The opposite configuration is also possible with two or more layers in the central area and only one on the sides. Such a liner may be advantageous for menstrual use or for delivery of medicaments.

More sophisticated types of liners may incorporate treatments of lotions or medicaments to improve the environment near the skin or to actually improve skin health. Such treatments include aloe, vitamin E, baking soda and other preparations as may be known or developed by those skilled in the art.

The core portion of a personal care product is designed to absorb liquids and secondarily to contain solids. The core, known also as an absorbent core, a retention layer, and the like, may be made with pulp and/or superabsorbent materials. These materials absorb liquids quite quickly and efficiently in order to minimize leakage. Core materials may be made according to a number of processes including the coform process, airlaying, and bonding and carding and should be between 50 and 200 gsm, with regard to basis weight.

Various other layers may be included in some personal care products. These include surge layers, usually placed between the liner and core and designed, as the name suggests, to contain large surges of liquid so that the core may absorb it over time. Distribution layers also are included in many personal care products. Distribution layers are usually located next to the core and accept liquid from the surge or liner layer and distribute it to other areas of the core. In this manner, rather than absorbing liquid exclusively in the vicinity of the target area, more of the absorbent core is used.

Synthetic fibers include those made from polyolefins, polyamides, polyesters, rayon, acrylics, superabsorbents, LYOCELL regenerated cellulose and any other suitable synthetic fibers known to those skilled in the art. Many polyolefins are available for fiber production, for example polyethylenes such as Dow Chemical's ASPUN 6811A linear low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's ESCORENE PD 3445 polypropylene and Montell Chemical Co.'s PF304. Other polyolefins are also available.

Natural fibers include wool, cotton, flax, hemp and wood pulp. Wood pulps include standard softwood fluffing grade such as CR-1654 (US Alliance Pulp Mills, Coosa, Ala.). Pulp may be modified in order to enhance the inherent characteristics of the fibers and their processability. Curl may be imparted to the fibers by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylated compounds such as urea or urea derivatives, dialdehydes such as maleic anhydride, non-methylated urea derivatives, citric acid or other polycarboxylic acids. Some of these agents are less preferable than others due to environmental and health concerns. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HP2 pulp and still another is IP Supersoft from International Paper Corporation. Suitable rayon fibers are 1.5 denier Merge 18453 fibers from Acordis Cellulose Fibers Incorporated of Axis, Ala.

Superabsorbents that may be useful in the present inventions can be chosen from classes based on chemical structure as well as physical form. Superabsorbents may be based on chemistries that include but are not limited to acrylic acid, iso-butylene/maleic anhydride, polyethylene oxide, carboxy-methyl cellulose, poly vinyl pyrrolidone, and poly vinyl alcohol. The superabsorbents may range in rate from slow to fast. The superabsorbents may be in the form of foams, macroporous or microporous particles or fibers, may have fuzzy or fibrous coatings or morphology. The superabsorbents may be in the shape of ribbons, particles, fibers, sheets or films. An exemplary superabsorbent may be obtained from Stockhausen, Inc and is designated as FAVOR 880.

Binders may also be used in structures to help provide mechanical integrity and stabilization. Binders include fiber, liquid or other binder means which may be thermally activated. Preferred fibers for inclusion are those having a relative melting point such as polyolefin fibers. Lower melting point polymers provide the ability to bond nonwoven fabric together at fiber crossover points upon the application of heat. In addition, fibers having a lower melting polymer, like conjugate and biconstituent fibers are suitable for use as binders. Exemplary binder fibers include conjugate fibers of polyolefins, polyamides and polyesters like the sheath core conjugate fibers available from KoSa Inc. (Charlotte, N.C.) under the designation T-255 and T-256. A suitable liquid binder is KYMENE 557LX available from Hercules Inc.

Figure 1:
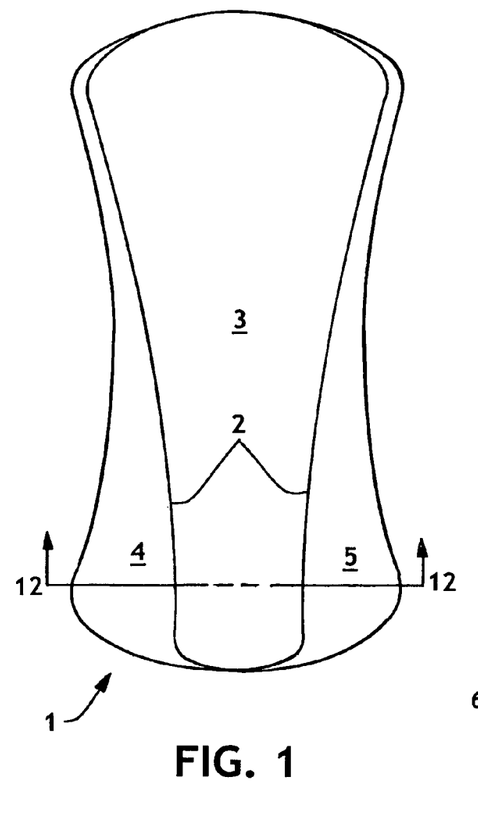
FIG. 1 is a top view of a dual-use pantiliner made in accordance with the invention.

The instant invention is a convertible, disposable pantiliner that may be used with conventional panties or with thong panties. The pantiliner 1, as shown in FIG. 1, has a slightly "hourglass" shape. It has a single line of embossing 2 corresponding approximately to the shape of a thong panty, that is used for folding the pantiliner and that defines three separate areas of the pantiliner. The central area 3 is in absorbent service when the pantiliner is applied to either style of panty. The periphery includes side areas 4, 5 that are in absorbent service when the pantiliner is applied to a conventional, hourglass-shaped panty but are folded under the panty along the fold (embossing) lines 2 when used with a thong panty. A cross-sectional line 12-12 forms the basis of FIG. 7, which illustrates a cross-sectional view of this Figure. As discussed below in relation to FIG. 2, it is possible to have additional lines of embossing for folding on either side of the single line shown in FIG. 1. These multiple lines may be added to the single line in increments of two for an odd number of as many as eleven total fold lines, thus allowing the consumer to adjust the product to fit her needs. Even more fold lines may be added to the product, but the incremental utility of such variations is not believed to be compelling. Such changes and variations are intended to be within the scope of the invention.

Figure 2:
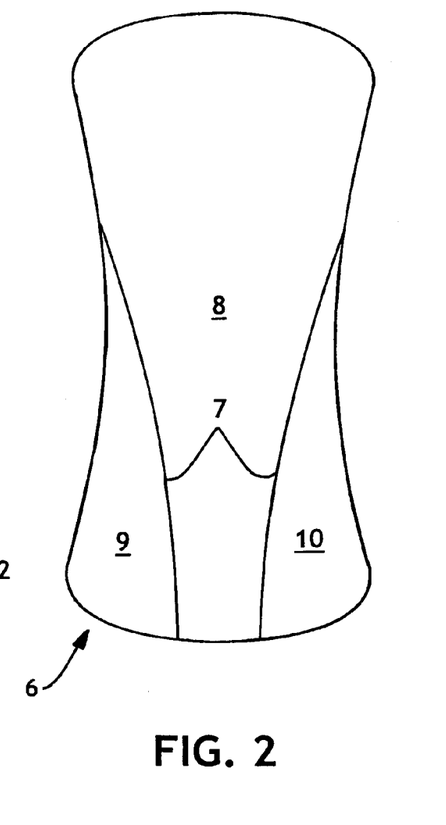
FIG. 2 is a top view of an alternate embodiment of a dual-use pantiliner made in accordance with the invention.
Figure 3:
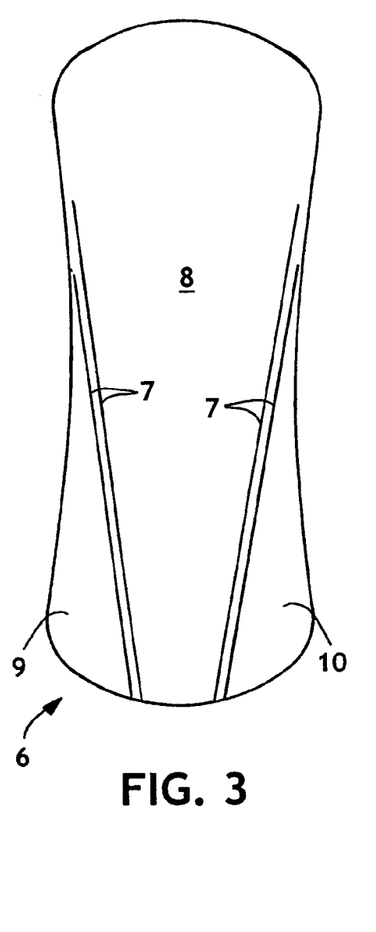
FIG. 3 is a top view of an alternate embodiment of a dual-use pantiliner made in accordance with the invention.
Figure 4:
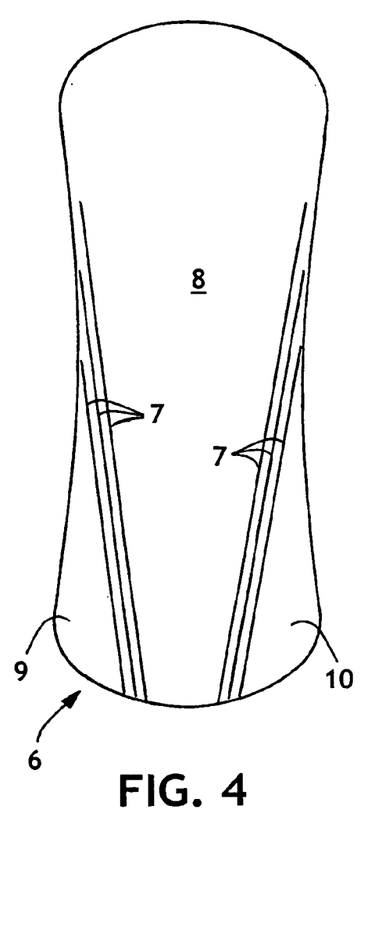
FIG. 4 is a top view of an alternate embodiment of a dual-use pantiliner made in accordance with the invention.
Figure 5:
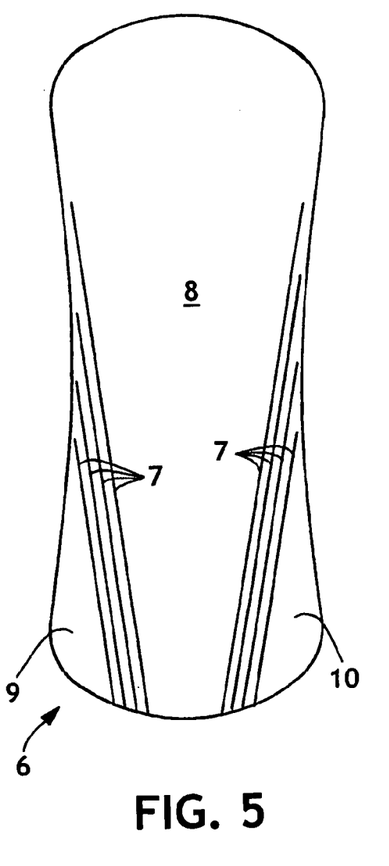
FIG. 5 is a top view of an alternate embodiment of a dual-use pantiliner made in accordance with the invention.
Figure 6:
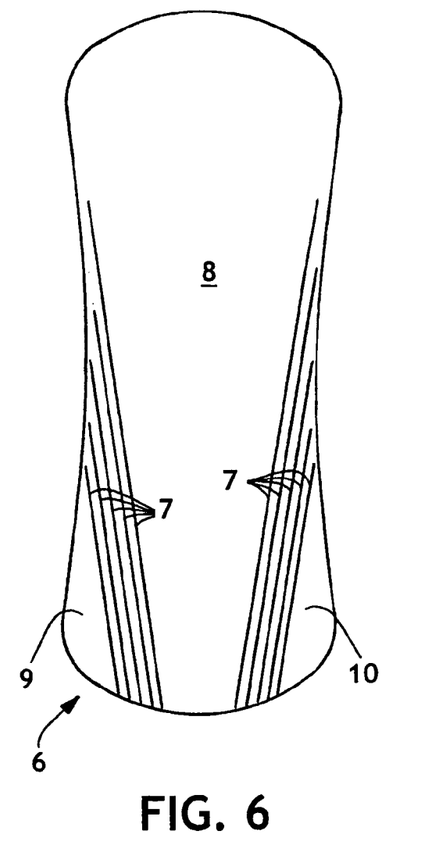
FIG. 6 is a top view of an alternate embodiment of a dual-use pantiliner made in accordance with the invention.

FIG. 2 shows a slightly different configuration of a pantiliner of this invention having an hourglass shape. The pantiliner 6, has two embossing lines 7, defining the central area 8, and side areas 9, 10. In FIG. 2, the lines of embossing 7 coincide with the outer edge of the pantiliner in some areas. FIGS. 3 through 6 show a configuration similar to that of FIG. 2, the difference being the number of fold or embossing lines increases by two for an even number of four to ten total lines, with half of the total on each side of the pantiliner. Multiple fold lines allow the pantiliner of this invention to be folded appropriately for thong panties of different sizes, thus allowing one convertible pantiliner product to serve the needs of many consumers. Multiple fold lines permit the consumer to choose which fold lines to use so that the width of the folded pantiliner best meets her needs.

Figure 7:
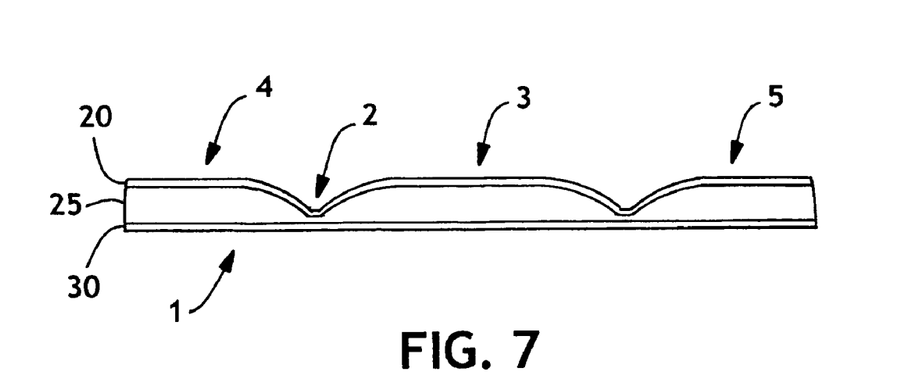
FIG. 7 is a cross-sectional view of the dual use pantiliner in accordance with FIG. 1 taken along lines 12-12.
Figure 8:
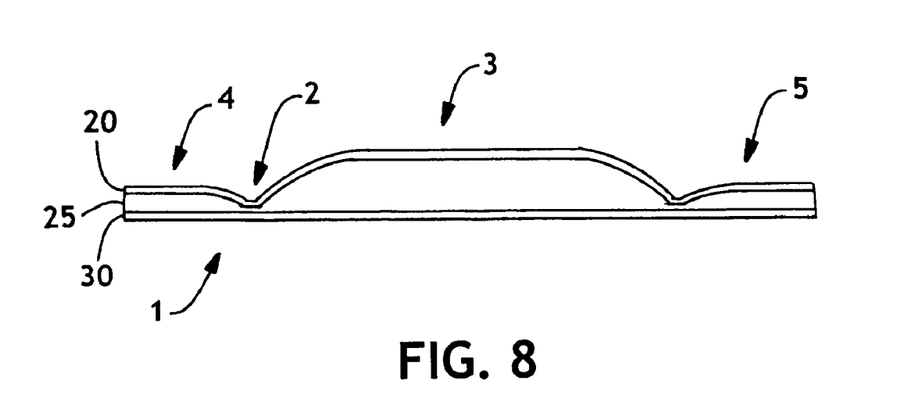
FIG. 8 is a cross-sectional view of an alternative embodiment of FIG. 1.

FIG. 7 illustrates a cross-sectional view of the dual-use pantiliner in accordance with FIG. 1 taken along lines 12-12. As can be seen in the Figure, the dual-use pantiliner 1 includes a top liner layer 20, which is placed against a wearer's skin, a core layer 25, designed to absorb liquids and secondarily contain solids, and a liquid impervious baffle or outer cover 30. Embossing lines 2 are embedded in the pantiliner. FIG. 8 illustrates an alternative embodiment of FIG. 2 in which the side areas 9 and 10 are thinner than the central area 8.

It should be noted that variations in the shape and size of the central and side areas to adjust to various hourglass and thong panty designs are considered to be within the ability of those skilled in the art. The invention is, however, distinct from conventional "winged" pantiliners as the invention is convertible for use in hourglass or thong panties. The wings on such conventional products are centrally located and are solely for attachment to the panty.

In another aspect of the invention, the side areas 4, 5, 9, and 10 may be made from material that is thinner than that of the central areas 3 and 8. The reason for this relative thinness is so that the side areas 4, 5, 9 and 10, when folded, do not make the pantiliner uncomfortably thick where the side areas 4, 5, 9 and 10 and the respective central areas 3 and 8 overlap.

Adhesive may be applied to the backing of the pantiliner to keep it in place while in use. The adhesive may be applied in any effective pattern. The adhesive may, for example, be applied as a narrow strip down the center, a wide strip covering the pantiliner in a rectangular shape with a width equal to the width of the pantiliner at its narrowest point, or may cover the entire pantiliner backing. A narrower strip of adhesive is advisable for more breathable embodiments since the adhesive tends to detract from breathability. If the adhesive is applied as a narrow strip in the center area 3, additional adhesive may be applied to the backing under the side areas 4, 5. A detachable paper is applied to the adhesive on the side opposite that of the baffle. The detachable paper is removed from the adhesive by the user prior to application of the pantiliner to the panty.

A particularly suitable core material for the practice of this invention may be produced according to U.S. Pat. No. 5,284,703. This patent concerns the hydraulic entanglement of pulp with a continuous filament substrate to produce an absorbent fabric. The substrate is preferably a nonwoven spunbond fabric and the pulp is more than 70 weight percent of the final absorbent, and a binder may be present. In the process of this patent, the nonwoven substrate is produced by conventional means such as meltblowing or spunbonding using any polymer known to be appropriate for such processes. The fibers thus formed may be single polymer or conjugate (bicomponent) fibers and may be round or of virtually any shape. The nonwoven is thermally point bonded with a total bond area of less than about 30 percent and has a uniform bond density greater than about 100 bonds per square inch (15.5 bonds per square cm). An exemplary point bond pattern for this process is known as the 714 pattern and is discussed above. On top of the nonwoven fabric is placed a pulp layer made by conventional papermaking means from a uniform dilute suspension of pulp fibers typically supplied by a headbox, deposited via a sluice, and de-watered. The nonwoven and pulp layers may be supported on a foraminous belt while they are subjected to a high pressure hydraulic entangling process. In hydraulic entangling, fluid (usually water) is directed at high pressure through orifices to form columnar jets that directly impinge upon the pulp fibers and drive the pulp fibers into and partially through the nonwoven substrate. A vacuum may be located beneath the foraminous support web so that excess fluid may be withdrawn from the hydraulically entangled composite matrix. After entanglement, the composite maybe transferred to a non-compressive drying operation. It may further be desired to subject the composite to finishing or post-treatment steps to impart particular properties. The composite may, for example, be creped, lightly calendered or brushed to modify the surface, or chemical treatments like dyes, adhesives and the like may be applied.

Embossing of the lines 2 on the pantiliner 1 may be done by any conventional means. Particularly suitable methods include the application of heat and pressure for short periods of time. It is preferred that the embossing not penetrate the baffle of the pantiliner so as to produce apertures or other openings for the flow of liquid, as this may result in the staining of the wearer's garments. It is also desired that the side areas 4, 5 not be detachable from the central area 3. Embossing through the baffle may make the detachment of the side areas 4, more likely since it may perforate the line of embossing 2. Such perforation is to be avoided. The embossing of lines onto the pantiliner should be performed at a temperature such that these negative effects are avoided. This temperature will depend upon the materials of construction of the pantiliner but should be between 40 and 80° C. for the materials commonly used in pantiliner production. Its believed that the embossing of the pantiliner also serves to improve the water repellency of the lines of embossing 2, making runoff from the pantiliner less likely.

EXAMPLE

Two layers of 60 gsm material made from nonwoven fibers and pulp were combined to produce the core for a pantiliner. The layers or material were made according to U.S. Pat. No. 5,284,703 and contained 79 weight percent pulp and 21 percent spunbond fibers.

The nonwoven layers were made from Exxon's ESCORENE PD 3445 polypropylene spunbond fibers of 2 denier at a basis weight of 13.6 gsm per layer.

The pulp layer was made from bleached softwood kraft pulp according to conventional papermaking means.

The nonwoven and pulp layers were hydraulically entangled using jets of water and the composite was dried by multiple drum dryers at temperatures of 50 to 127° C. and a Yankee dryer at 102° C.

A baffle was used as the layer below the core and was a polyethylene film having a thickness of 1.7 mils. The liner was a 21 gsm thermally bonded carded web of synthetic polymer fibers. The pantiliner was embossed with the pattern of FIG. 1 at a temperature of 80° C. and a pressure of 70 psi.

This product was produced in the hourglass shape of a pantiliner as shown in FIG. 1 so that it could be applied to a conventional panty with this shape. It was found that this product was easily converted into use as a thong pantiliner by bending the side areas downward and wrapping them around the panty.

As will be appreciated by those skilled in the art, changes and variations to the invention are considered to be within the ability of those skilled in the art. Such changes and variations are intended by the inventors to be within the scope of the invention.

What is claimed is:

1. A convertible pantiliner including a liner, a baffle and an absorbent core therebetween, said pantiliner further comprising at least one embossed fold line defining a central area and two he side areas, said central area having two longitudinal ends, with a first longitudinal end being wider than said second longitudinal end, and wherein said pantiliner may be adjusted in size, depending on panty size, by folding said pantiliner along said at least one embossed fold line so as to allow said periphery side areas to be positioned under a panty prior to, and while said pantiliner is in use, and wherein said at least one embossed fold line does not penetrate said baffle.

2. The pantiliner of claim 1 wherein said at least one embossed fold line is a line of embossing produced at a temperature of between about 40 and 80° C.

3. The pantiliner of claim 1 wherein said absorbent core is selected from the group consisting of spunbond webs, meltblown webs, bonded-carded webs, airlaid webs, and laminates and composites thereof.

4. The pantiliner of claim 1 wherein said side areas are thinner than said central area.

5. The pantiliner of claim 1 wherein said at least one fold line includes two fold lines.

6. The pantiliner of claim 1 wherein said at least one fold line includes four fold lines.

7. The pantiliner of claim 1 wherein said at least one fold line includes six fold lines.

8. The pantiliner of claim 1 wherein said at least one fold line includes eight fold lines.

9. The pantiliner of claim 1 wherein said at least one fold line includes ten fold lines.

10. A convertible pantiliner comprising a liquid permeable liner, a liquid impervious baffle, and an absorbent core positioned therebetween, said absorbent core comprising more than 70 weight percent pulp hydroentangled with spunbond polypropylene fibers, said pantiliner further comprising a periphery and at least one embossed fold line which does not penetrate said baffle, wherein said pantiliner may be adjusted in size, depending on panty size, by folding said pantiliner along said at least one embossed fold line, so as to allow said periphery to be positioned under a panty thereby creating a pantiliner on a panty including a first longitudinal end that is wider than a second longitudinal end.

11. The pantiliner of claim 10 wherein said baffle is breathable.

12. The pantiliner of claim 10 wherein said core has a basis weight between 50 and 200 gsm.

13. The pantiliner of claim 10 further comprising a treatment on said liquid permeable liner.

14. The pantiliner of claim 10 wherein said at least one fold line includes two fold lines.

15. The pantiliner of claim 10 wherein said at least one fold line includes fourfold lines.

16. The pantiliner of claim 10 wherein said at least one fold line includes six fold lines.

17. The pantiliner of claim 10 wherein said at least one fold line includes eight fold lines.

18. The pantiliner of claim 10 wherein said at least one fold line includes ten fold lines.

* * * * *